United States Patent
Ghose et al.

(10) Patent No.: US 12,237,086 B2
(45) Date of Patent: Feb. 25, 2025

(54) METHOD AND SYSTEM FOR DIGITAL BIOMARKERS PLATFORM

(71) Applicant: Tata Consultancy Services Limited, Mumbai (IN)

(72) Inventors: Avik Ghose, Kolkata (IN); Avijit Samal, Kolkata (IN); Nasimuddin Ahmed, Kolkata (IN); Shivam Singhal, Gurgaon (IN); Karan Bhavsar, Thane (IN); Vivek Chandel, Gurgaon (IN); Sundeep Khandelwal, Noida (IN); Harsh Vishwakarma, Thane (IN); Bhaskar Pawar, Thane (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 484 days.

(21) Appl. No.: 17/653,248

(22) Filed: Mar. 2, 2022

(65) Prior Publication Data
US 2022/0344055 A1  Oct. 27, 2022

(30) Foreign Application Priority Data
Mar. 20, 2021 (IN) .............................. 202121011956

(51) Int. Cl.
*G16H 50/30* (2018.01)
*G06F 16/178* (2019.01)
(Continued)

(52) U.S. Cl.
CPC .......... *G16H 50/30* (2018.01); *G06F 16/1794* (2019.01); *G06F 16/258* (2019.01); *G16H 40/67* (2018.01)

(58) Field of Classification Search
CPC ...... G16H 50/30; G16H 40/67; G06F 16/258; G06F 16/1794
See application file for complete search history.

(56) References Cited

U.S. PATENT DOCUMENTS 8,725,462 B2    5/2014  Jain et al.
2016/0359917 A1* 12/2016 Rao .................... H04L 41/0894
(Continued)

OTHER PUBLICATIONS

Brasier N. et al., "Device- and Analytics-Agnostic Infrastructure for Continuous Inpatient Monitoring: A Technical Note," Digital biomarkers, 2020, Karger, https://www.karger.com/Article/PDF/509279.
(Continued)

*Primary Examiner* — Kris E Mackes
*Assistant Examiner* — Lin Lin M Htay
(74) *Attorney, Agent, or Firm* — FINNEGAN, HENDERSON, FARABOW, GARRETT & DUNNER LLP

(57) ABSTRACT

Non-communicable diseases (NCDs) are the pandemics of modern era and are generating huge impact in the modern society. Conventional methods are inaccurate due to a challenge in handling data from heterogenous sensors. The present disclosure is capable of tracking fitness parameters of a user even with heterogenous sensors. Initially, the system receives a raw data from a plurality of heterogenous sensors associated with the user. The raw data is further transformed into a metadata format associated with the corresponding sensor. The transformed data is temporally aligned based on a time based slotting. An algorithm pipeline corresponding to a disorder to be analyzed is selected from a Directed Acyclic Graph (DAG) based on a sensor metadata and a plurality of algorithm metadata corresponding to a plurality of algorithms stored in an algorithm database and an algorithm pipeline. The corresponding disorder is analyzed using the algorithm pipeline.

13 Claims, 7 Drawing Sheets

(51) Int. Cl.
    *G06F 16/25*     (2019.01)
    *G16H 40/67*     (2018.01)

(56) References Cited

U.S. PATENT DOCUMENTS

| | | | |
|---|---|---|---|
| 2020/0258601 A1* | 8/2020 | Lau | G16H 50/20 |
| 2021/0090694 A1* | 3/2021 | Colley | G16H 15/00 |
| 2021/0151192 A1* | 5/2021 | Lucas | G06Q 40/08 |

OTHER PUBLICATIONS

Page, A. et al., "Visualization of Health Monitoring Data acquired from Distributed Sensors for Multiple Patients," Global Communications Conference (Globecom), Dec. 2015, IEEE, https://www.researchgate.net/publication/284174301_Visualization_of_Health_Monitoring_Data_Acquired_from_Distributed_Sensors_for_Multiple_Patients/link/564dee6408aefe619b0ee8f3/download.

Mezghani, E. et al., "A Semantic Big Data Platform for Integrating Heterogeneous Wearable Data in Healthcare," Journal of Medical Systems, Oct. 2015, vol. 39 (12), Springer, https://www.researchgate.net/publication/283815607_A_Semantic_Big_Data_Platform_for_Integrating_Heterogeneous_Wearable_Data_in_Healthcare/link/56e0890008aee77a15fe9a89/download.

Ranjan, Y. et al. "Radar-base: An Open Source mHealth Platform for Collecting, Monitoring and Analyzing Data Using Sensors, Wearables, and Mobile Devices," Journal of Medical Systems Date: Aug. 2018, vol. 7 (8), NCBI, https://www.researchgate.net/publication/327334362_RADAR-base_An_Open_Source_mHealth_Platform_for_Collecting_Monitoring_and_Analyzing_data_Using_Sensors_Wearables_and_Mobile_Devices/link/5c12408792851c39ebe99f19/download.

* cited by examiner

METHOD AND SYSTEM FOR DIGITAL BIOMARKERS PLATFORM

PRIORITY CLAIM

This application claims priority under 35 U.S.C. § 119 from Indian Application No. 202121011956, filed on Mar. 20, 2021. The entire contents of the aforementioned application are incorporated herein by reference.

TECHNICAL FIELD

The disclosure herein generally relates to the field of application security and, more particular, to a method and system for digital biomarkers platform.

BACKGROUND

Non-communicable diseases (NCDs) are the pandemics of modern era and are generating huge impact in the modern society. The fast changing socioeconomical and structural factors such as rapid urbanization coupled with unhealthy lifestyles have fueled the NCD crisis that kills millions of people. However, digital health interventions have shown to improve outcomes with positive impact on NCDs. Nowadays, wearables are playing an important role as personal monitors for health and fitness today, tracking parameters like step count, heart rate and activity. However, the efficacy of digital interventions is significantly influenced by the patient's engagement with the instrument.

Conventional methods are inaccurate due to a challenge in handling data from heterogenous sensors. Further, many conventional approaches losses accuracy due to patient's engagement with the instrument, which is a major challenge as long-term adherence, with a vast majority rapidly losing interest and subsequently stopping using the wearable device. Hence there is a challenge is monitoring and measuring NCDs with heterogeneous sensors.

SUMMARY

Embodiments of the present disclosure present technological improvements as solutions to one or more of the above-mentioned technical problems recognized by the inventors in conventional systems. For example, in one embodiment, a method for digital biomarkers platform is provided. The method includes receiving, by one or more hardware processors, a raw data from a plurality of sensors associated with a user, wherein the plurality of sensors are heterogeneous. Further, the method includes transforming by the one or more hardware processors, the raw data into a sensor metadata format associated with a corresponding sensor. Furthermore, the method includes obtaining by the one or more hardware processors, a temporally aligned data by performing a time based slotting on the transformed data. Furthermore, the method includes obtaining by the one or more hardware processors, the sensor metadata corresponding to the temporally aligned data from a database based on a comparison between the temporally aligned data and the sensor metadata. Furthermore, the method includes selecting by the one or more hardware processors, an algorithm pipeline corresponding to a disorder to be analyzed from a Directed Acyclic Graph (DAG) based on the sensor metadata and a plurality of algorithm metadata corresponding to a plurality of algorithms stored in an algorithm database. Finally, the method includes analyzing by the one or more hardware processors, the disorder associated with the user based on the selected algorithm pipeline.

In another aspect, a system for digital biomarkers platform is provided. The system includes at least one memory storing programmed instructions, one or more Input/Output (I/O) interfaces, and one or more hardware processors operatively coupled to the at least one memory, wherein the one or more hardware processors are configured by the programmed instructions to receive a raw data from a plurality of sensors associated with a user, wherein the plurality of sensors are heterogeneous. Further the one or more hardware processors are configured by the programmed instructions to transform the raw data into a sensor metadata format associated with a corresponding sensor. Furthermore, the one or more hardware processors are configured by the programmed instructions to obtain a temporally aligned data by performing a time based slotting on the transformed data. Furthermore, the one or more hardware processors are configured by the programmed instructions to obtain the sensor metadata corresponding to the temporally aligned data from a database based on a comparison between the temporally aligned data and the sensor metadata. Furthermore, the one or more hardware processors are configured by the programmed instructions to select an algorithm pipeline corresponding to a disorder to be analyzed from a Directed Acyclic Graph (DAG) based on the sensor metadata and a plurality of algorithm metadata corresponding to a plurality of algorithms stored in an algorithm database. Finally, the one or more hardware processors are configured by the programmed instructions to analyze the disorder associated with the user based on the selected algorithm pipeline.

In yet another aspect, a computer program product including a non-transitory computer-readable medium having embodied therein a computer program for digital biomarkers platform is provided. The computer readable program, when executed on a computing device, causes the computing device to receive a raw data from a plurality of sensors associated with a user, wherein the plurality of sensors are heterogeneous. Further the computer readable program, when executed on a computing device, causes the computing device to transform the raw data into a sensor metadata format associated with a corresponding sensor. Further the computer readable program, when executed on a computing device, causes the computing device to obtain a temporally aligned data by performing a time based slotting on the transformed data. Furthermore, the computer readable program, when executed on a computing device, causes the computing device to obtain the sensor metadata corresponding to the temporally aligned data from a database based on a comparison between the temporally aligned data and the sensor metadata. Furthermore, the computer readable program, when executed on a computing device, causes the computing device to select an algorithm pipeline corresponding to a disorder to be analyzed from a Directed Acyclic Graph (DAG) based on the sensor metadata and a plurality of algorithm metadata corresponding to a plurality of algorithms stored in an algorithm database. Finally, the computer readable program, when executed on a computing device, causes the computing device to analyze the disorder associated with the user based on the selected algorithm pipeline.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
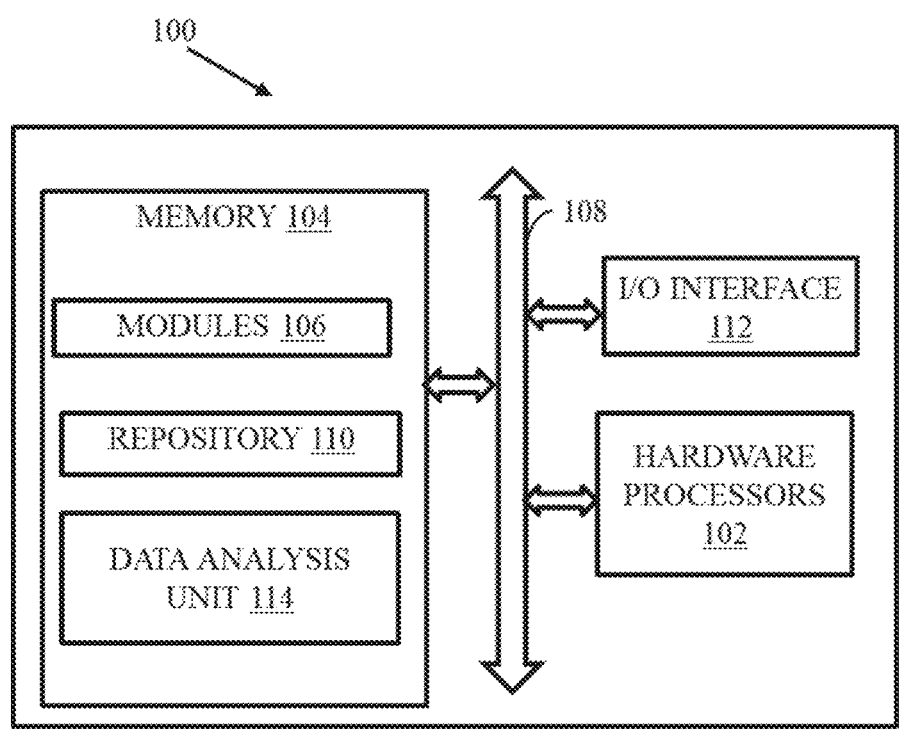
FIG. 1 is a functional block diagram of a system for digital biomarkers platform, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

Embodiments herein provide a method and system for digital biomarkers platform analyzes a disorder associated with a patient or a user. The method and system for digital biomarkers platform is capable of tracking fitness parameters of a user including a step count, a distance walked, an average walking speed, an inactivity detection, a step-based activity classification (including upstairs and downstairs), and a number of calories expended. Initially, the system receives a raw data from a plurality of heterogenous sensors associated with the user. The raw data is further transformed into a metadata format associated with the corresponding sensor. The transformed data is temporally aligned based on a time based slotting. Further, the sensor metadata corresponding to the temporally aligned data is obtained from a database. An algorithm pipeline corresponding to a disorder to be analyzed is selected from a Directed Acyclic Graph (DAG) based on the sensor metadata and a plurality of algorithm metadata corresponding to a plurality of algorithms stored in an algorithm database and an algorithm pipeline. The corresponding disorder is analyzed using the algorithm pipeline.

Referring now to the drawings, and more particularly to FIGS. 1 through 7, where similar reference characters denote corresponding features consistently throughout the figures, there are shown preferred embodiments and these embodiments are described in the context of the following exemplary system and/or method.

FIG. 1 is a functional block diagram of a system 100 for digital biomarkers platform, according to some embodiments of the present disclosure. The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, a plurality of sensors and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting a number of computing systems with one another or to another server computer. The I/O interface 112 may include one or more ports for connecting a number of devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a plurality of modules 106 and a data analysis unit 114. The memory 104 also includes a data repository (or repository) 110 for storing data processed, received, and generated by the plurality of modules 106 and the data analysis unit 114.

The plurality of modules 106 include programs or coded instructions that supplement applications or functions performed by the system 100 for digital biomarkers platform. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for digital biomarkers platform.

The data repository (or repository) 110 may include a plurality of abstracted piece of code for refinement and data that is processed, received, or generated as a result of the execution of the plurality of modules in the module(s) 106 and the modules associated with data analysis unit 114. In an embodiment, modules such as data ingestion module, an orchestration module, an algorithm pipeline selection module, a disorder analysis module and a visualization module are present inside data analysis unit 114. The data repository may also include a plurality of algorithms, a plurality of sensor metadata and a plurality of algorithm metadata.

Although the data repository 110 is shown internal to the system 100, it will be noted that, in alternate embodiments, the data repository 110 can also be implemented external to the system 100, where the data repository 110 may be stored within a database (not shown in FIG. 1) communicatively coupled to the system 100. The data contained within such external database may be periodically updated. For example, new data may be added into the database (not shown in FIG. 1) and/or existing data may be modified and/or non-useful data may be deleted from the database (not shown in FIG. 1). In one example, the data may be stored in an external system, such as a Lightweight Directory Access Protocol (LDAP) directory and a Relational Database Management System (RDBMS).

Figure 2:
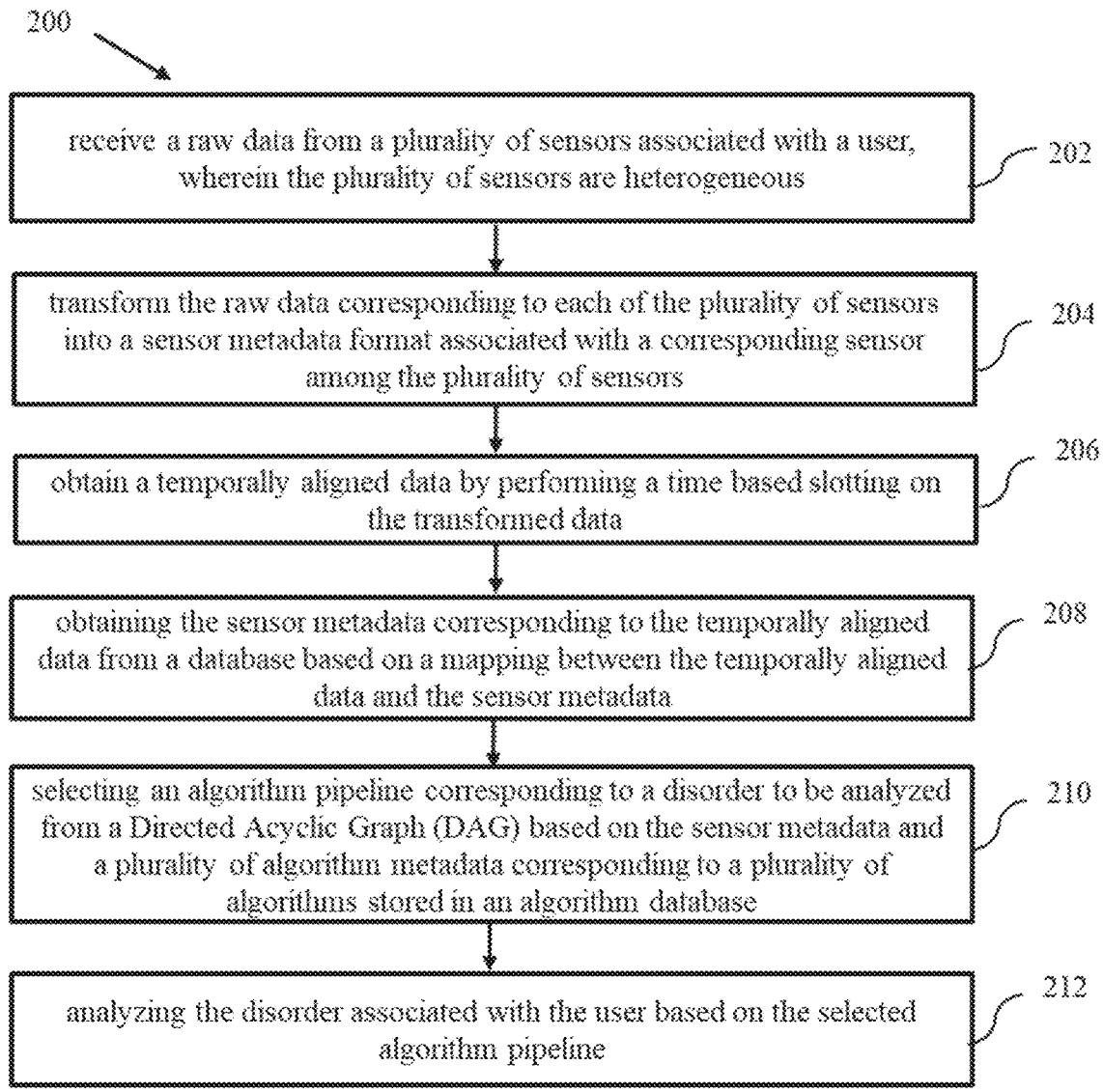
FIG. 2 is an exemplary flow diagrams for a method for digital biomarkers platform, implemented by the system of FIG. 1, in accordance with some embodiments of the present disclosure.

FIG. 2 is exemplary flow diagram depicting a method 200 for a processor implemented method for digital biomarkers platform implemented by the system of FIG. 1 according to some embodiments of the present disclosure. In an embodiment, the system 100 includes one or more data storage devices or the memory 104 operatively coupled to the one or more hardware processor(s) 102 and is configured to store instructions for execution of steps of the method 200 by the one or more hardware processors 102. The steps of the method 200 of the present disclosure will now be explained with reference to the components or blocks of the system 100 as depicted in FIG. 1 and the steps of flow diagram as depicted in FIG. 2A. The method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communication network. The order in which the method 200 is described is not intended to be construed as a limitation, and any number of the described method blocks can be combined in any order to implement the method 200, or an alternative method. Furthermore, the method 200 can be implemented in any suitable hardware, software, firmware, or combination thereof.

At step 202 of the method 200, the one or more hardware processors 102 receive a raw data from a plurality of sensors associated with a user, wherein the plurality of sensors are heterogeneous. For example, the plurality of sensors includes an accelerometer, a gyroscope, a barometer, a Kinect® depth camera and a PhotoPlethysmoGram (PPG). The raw data format includes a time series data, a comma separated values, a string data, a numerical, a Boolean data, a list, a plurality of objects, a plurality of videos and a plurality of images.

In an embodiment, the present disclosure utilizes smartwatch for capturing the user's physiological, environmental and motion signatures in a continuous and unobtrusive manner. Most of the smartwatches available commercially these days are equipped with a variety of built-in sensors, which can provide raw data with high precision and accuracy. For different operating systems, different sensor frameworks are available which can be used to access this raw sensor data. The raw data is stored as a NoSQL document in the database as input data batches.

At step 204 of the method 200, the one or more hardware processors 102 transform the raw data into a sensor metadata format associated with a corresponding sensor. The sensor metadata includes a type of data generated by the corresponding sensor, a sampling frequency, a buffering capacity and a model associated with the corresponding sensor. The terms "schema" and "metadata" are used interchangeably throughout the document.

Since the method disclosed herein allows data collection from multiple heterogenous sensors with varying data formats, it needs device data adaptors to translate the unknown source data format to a known uniform data format, thus making the platform extensible for adding new devices and sensors with varying data formats.

For example, the metadata or schema associated with the accelerometer data is a plurality of arrays including is (timestamp), x, y, and z (force along respective axis). The corresponding transformed data is "ts": [1600089224599, 1600089224607, 1600089224620, 1600089224627, . . . ], "X": [1.271, 1.261, 1.251, 1.364, . . . ], "y": [2.606, 2.713, 2.838, 2.682, . . . ], "z": [9.361, 9.327, 9.356, 9.385, . . . ].

The present disclosure simultaneously transmits the sensed data to the cloud at regular time-intervals. Multi-threading is used to prevent any sensor data loss during data transmission being performed by the application. In an embodiment, data sampling rate of 100 Hz is used for the accelerometer, the gyroscope and the PPG sensors, whereas for barometer, data is sampled at 10 Hz. The sampled data is transferred to the cloud in the form of packets, with each packet containing 10 seconds data. Along with the sensor data, a unique device ID is also appended in each packet, which enables identification of the smartwatch from which the data packet has been received at the cloud. MD5 message-digest algorithm is used to generate the device ID by passing Wi-Fi MAC address of the smartwatch as an input to the hash function. Hashing algorithm is used for ensuring data security. Sensor data packets received on the cloud are then used to compute the required parameters with minimal latency.

At step 206 of the method 200, the one or more hardware processors 102 obtain a temporally aligned data by performing a time based slotting on the transformed data.

In an embodiment, the transformed data is sliced up column wise to create separate documents at the time of storage to enable random access to any part of the data as opposed to searching through all the rows.

At step 208 of the method 200, the one or more hardware processors 102 obtain the sensor metadata corresponding to the temporally aligned data from a database based on a comparison between the temporally aligned data and the sensor metadata.

At step 210 of the method 200, the one or more hardware processors 102 select an algorithm pipeline corresponding to a disorder to be analyzed from a Directed Acyclic Graph (DAG) based on the sensor metadata and a plurality of algorithm metadata corresponding to a plurality of algorithms stored in an algorithm database. The method of selecting the algorithm pipeline corresponding to the selected disorder to be analyzed from the Directed Acyclic Graph (DAG) based on the sensor metadata and a plurality of algorithm metadata includes the followings steps: (i) receiving the DAG comprising a plurality of nodes and a plurality of edges. Each of the plurality of nodes associated with the DAG represents an algorithm from the plurality of algorithms and each of the plurality of edges connecting two nodes indicates a dependency between a preceding node and a succeeding node. The DAG is associated with at least one entry point (ii) selecting an initial node corresponding to a first algorithm of the algorithm pipeline from the DAG based on a mapping between the corresponding sensor metadata and an algorithm metadata associated with each of the plurality of algorithms. The initial node is assigned as a current node. The algorithm metadata includes a data format, a preferred sampling rate, a minimum quantum of data needed for processing, an output data format, a description of method used by the corresponding algorithm (iii) obtaining the algorithm schema associated with a plurality of next nodes associated with the current node (iv) selecting a next node from the plurality of next nodes based on a comparison between an output associated with the current node and the algorithm schema associated with each of the plurality of next nodes. The selected next node is assigned as the current node. The DAG is traversed until reaching a leaf node. The leaf node is identified based on a next null pointer and (v) obtaining the algorithm pipeline based on the traversal path from the initial node to the leaf node.

In an embodiment, the method of constructing the DAG for a disorder from a plurality of disorders is explained as follows: Initially, a first algorithm corresponding to the disorder, the algorithm metadata associated with the first algorithm, an output associated with the first algorithm and the corresponding sensor metadata are received. The output associated with the first algorithm is predetermined. Further, an initial node is inserted into the DAG corresponding to the first algorithm based on a mapping between the algorithm metadata associated with the first algorithm and the corresponding sensor metadata associated with the corresponding disorder. The first algorithm is marked as visited and the initial node is assigned as a current node. Further, a second algorithm is selected from the plurality of algorithms based on a mapping between the output associated with the first algorithm, the corresponding sensor metadata and the algorithm metadata associated with a plurality of unvisited algorithms. Further, a second node corresponding to the second algorithm is generated when there is a mapping existing between the output associated with the first algorithm, the corresponding sensor metadata and at least one of the pluralities of unvisited algorithms. Finally, an edge is generated between the current node and the second node. The second node is assigned as the current node. The DAG construction is performed until a plurality of measurements associated with the corresponding disorder is satisfied. The plurality of measurements includes a heart-rate of the user, a step count or derived for example cardiac fatigue and a calorie.

At step 212 of the method 200, the one or more hardware processors 102 analyze the disorder associated with the user based on the selected algorithm pipeline.

The data analysis unit 114, when executed by one or more processors of the system 100 receive the raw data from the plurality of sensors associated with the user, wherein the plurality of sensors are heterogeneous. For example, the plurality of sensors includes the accelerometer, the gyroscope, the barometer and the PPG. The raw data format includes the time series data, the comma separated values, the string data, the numerical data, the Boolean data, the list, the plurality of objects, the plurality of videos and the plurality of images.

The PPG sensor is ubiquitous to every smartwatch available today. It enables a real-time monitoring of heart rate (HR) while performing various activities, with Breathing rate (BR) also possible to derive from then PPG signal. Process of respiration modulates the PPG signal with respect to its intensity, amplitude and frequency. These modulations, being very weak in power, can be extracted only from a good quality PPG signal. Commercial devices like smartwatches, smartphones etc. generate a noisy PPG when compared to professional dedicated devices like pulse oximeters. Further, in case of smartwatches, motion of the wrist further deteriorates the quality of PPG signal, rendering estimation of BR impossible. Hence, a plurality of periods of inactivity are detected on the watch. For these periods, a real-time breathing rate is calculated using Cardiac Care Pathway (C2P) method. Since the method disclosed herein is capable of detecting intensive activities like walking upstairs/downstairs, brisk walking and running, measures of BR before and after performing an intensive activity can provide, the method can provide a qualitative information regarding the fatigue induced, and insights into cardiopulmonary health of the subject to a medical professional.

The data analysis unit 114, when executed by one or more hardware processors 102 of the system 100 transform the raw data into a corresponding sensor metadata format associated with the corresponding sensor. The sensor metadata includes the type of data generated by the corresponding sensor, the sampling frequency, the buffering capacity and the model associated with the corresponding sensor. The sensor metadata includes the type of data generated by the corresponding sensor, the sampling frequency, the buffering capacity and the model associated with the corresponding sensor.

The data analysis unit 114, when executed by one or more hardware processors 102 of the system 100 obtain the temporally aligned data by performing a time based slotting on the transformed data.

For example, in case of wrist wearable devices, detection of steps is more challenging owing to the continuous relative motion of the wrist with respect to the vertical vector perpendicular to the transverse body plane while walking. Further, an accurate step count is targeted even in indoor scenarios where the walking trajectories vary in direction and step duration very frequently. This ambiguity can lead to accumulation of error in number of steps detected. The present disclosure deals with the ambiguity using a step detection method. The pseudocode for the step detection method is given below:

Pseudocode 1: Step detection method

```
1: global cpList =< empty > // List of validated peaks
2: global activeFreq = -1 // Latest step frequency
3: procedure VALIDATECONSISTENCY(pList,pPeak).
//(list of peaks to be validated, latest validated peak yet)
 4:    n ← length(pList)
 5:    if pPeak > 0 then //pPeak is set from a previous window
 6:        pList.prepend(pPeak)
 7:        n ← n + 1
 8:    end if
 9:    for 'p_i' in pList with i=1,2 ... n do
10:        stepFreq ← fs/(p_i - p_{i-1})// Step frequency
11:        if activeFreq < 0 then
12:            cpList.append(p_{i-1})
13:            cpList.append(p_i)
14:        else if (stepFreq ≥ activeFreq -dF) AND (stepFreq ≤ activeFreq + dF)
then
15:                cpList.append(p)
16:                if length(cpList)+1 ≥ dP then
17:                    onStepsDetected(cpList) // outputs valid steps
               through a callback
18:                end if
19:        else
20:            cpList.clear( )
21:            cpList.append(p_{i-1})
22:            cpList.append(p_i)
23:        end if
24:        activeFreq ← stepFreq
25:    end for
26: end procedure
```

The pseudocode for step detection method receives a set of peaks detected in the current window of accelerometer data (pList), and also the latest valid peak that has been hitherto detected (pPeak). pList represents sample numbers of all the peaks detected in the current window: pList={$p_0$, $p_2$, ... $p_i$, ..., $p_n$}. If the step detection method has started to operate on a new session, pPeak is not set, else pPeak is added as the $1^{st}$ member in the above expressed pList. For all the peaks, every pair of consecutive peaks is processed chronologically. For every pair of peaks represented by sample numbers $p_i$ and $p_{i+1}$ in pList, a step frequency is calculated as: stepFreq$_i$=fs/($p_{i+1}$-$p_i$). A check is performed whether stepFreq$_i$ lies within the range of value dF to stepFreq$_{i-1}$. If the check is passed, then stepFreq$_i$ is inserted into a list, cpList. Else, cpList is cleared, and both $p_i$ and $p_{i-1}$ are inserted to the list. If the length of cpList is found to be one greater than a certain value dP, then the peak $p_i$ is deemed as a peak representing an actual step, which is provided as an output by the algorithm before proceeding to check the remaining peaks $p_{i+1}$, $p_{i+2}$, $p_n$.

Figure 3A:
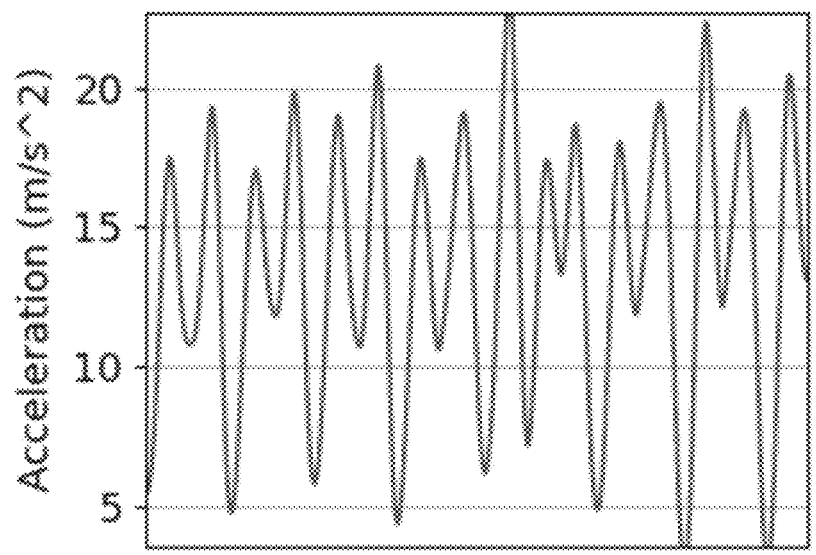
FIGS. 3A and 3B are graphs illustrating ambiguity in step signatures for a processor implemented method for digital biomarkers platform implemented by the system of FIG. 1 according to some embodiments of the present disclosure.
Figure 3B:
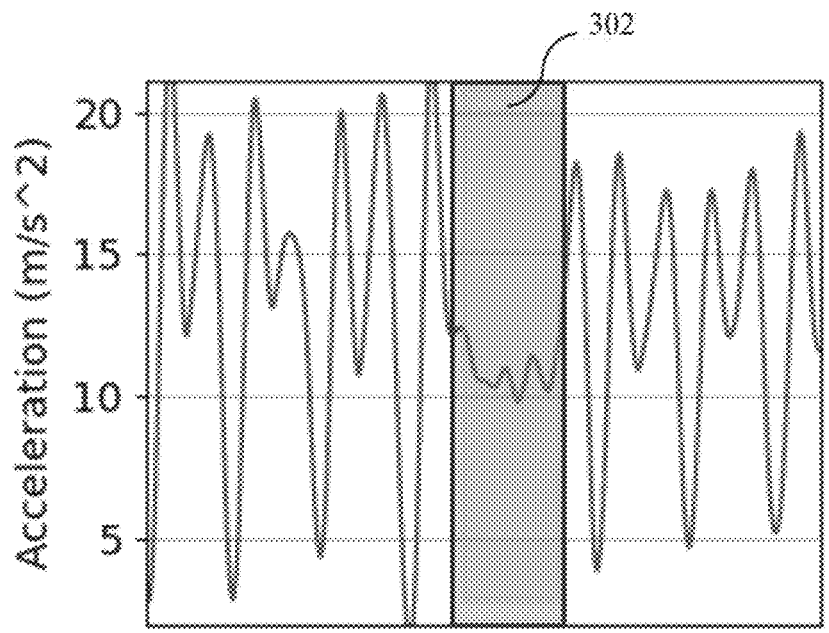

FIGS. 3A and 3B are graphs illustrating ambiguity in step signatures for a processor implemented method for digital biomarkers platform implemented by the system of FIG. 1 according to some embodiments of the present disclosure. FIG. 3A represents typical signal from a wrist-worn accelerometer while walking in a trajectory without any sharp turns. It is apparent that all the steps are recorded clearly in the signal represented by individual peaks. FIG. 3B represents the accelerometer signal while walking through a sharp turn in the trajectory (e.g. while walking in indoor environment). The shaded portion 302 of the FIG. 3B pertains to the section of the signal recorded while the turn is undertaken, where it can be seen that the clarity of the peaks representing the actual steps vanishes. If the system fails to detect steps taken while making sharp turns, then an appreciable error in overall step count can occur in sessions performed with multiple sharp turns, e.g. in indoor environments.

The data analysis unit 114, when executed by one or more hardware processors 102 of the system 100 obtain the sensor metadata corresponding to the temporally aligned data from a database or the repository based on a comparison between the temporally aligned data and the sensor metadata.

The data analysis unit 114, when executed by one or more hardware processors 102 of the system 100 select an algorithm pipeline corresponding to a disorder to be analyzed from a Directed Acyclic Graph (DAG) based on the sensor metadata and a plurality of algorithm metadata corresponding to a plurality of algorithms stored in an algorithm database. The method of selecting the algorithm pipeline corresponding to the selected disorder to be analyzed from the Directed Acyclic Graph (DAG) based on the sensor metadata and the plurality of algorithm metadata is explained using FIG. 4.

Figure 4:
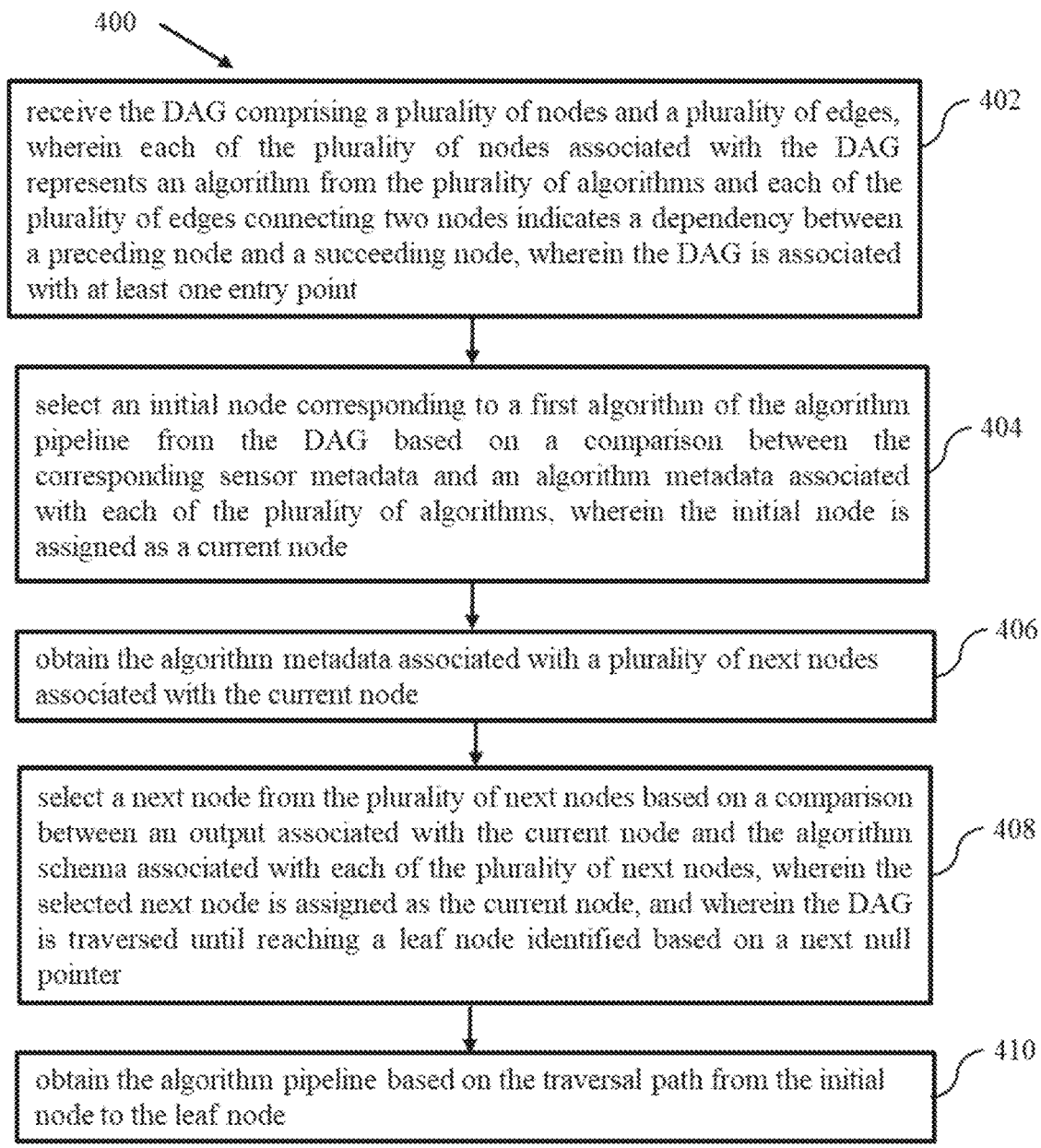
FIG. 4 is an exemplary flow diagram for a processor implemented method for selecting the algorithm pipeline in digital biomarkers platform implemented by the system of FIG. 1 according to some embodiments of the present disclosure.

FIG. 4 is an exemplary flow diagram of method 400 for a processor implemented method for selecting the algorithm pipeline in digital biomarkers platform implemented by the system of FIG. 1 according to some embodiments of the present disclosure.

Now referring to FIG. 4, at step 402 of method 400, the DAG comprising a plurality of nodes and a plurality of edges is received. Each of the plurality of nodes associated with the DAG represents the algorithm from the plurality of algorithms and each of the plurality of edges connecting two nodes indicates the dependency between the preceding node and the succeeding node. The DAG is associated with at least one entry. At step 404 of method 400, an initial node corresponding to a first algorithm of the algorithm pipeline is selected from the DAG based on the comparison between the corresponding sensor metadata and the algorithm metadata associated with each of the plurality of algorithms. The initial node is assigned as the current node. The algorithm metadata includes the data format, the preferred sampling rate, the minimum quantum of data needed for processing, the output data format, the description of method used by the corresponding algorithm. At step 406 of method 400, the algorithm schema associated with a plurality of next nodes associated with the current node is obtained. At step 408 of method 400, a next node is selected from the plurality of next nodes based on the comparison between an output associated with the current node and the algorithm schema associated with each of the plurality of next nodes. The selected next node is assigned as the current node and the DAG is traversed until reaching the leaf node. The leaf node is identified based on the next null pointer. At step 410 of method 400, the algorithm pipeline is obtained based on the traversal path from the initial node to the leaf node.

Figure 5:
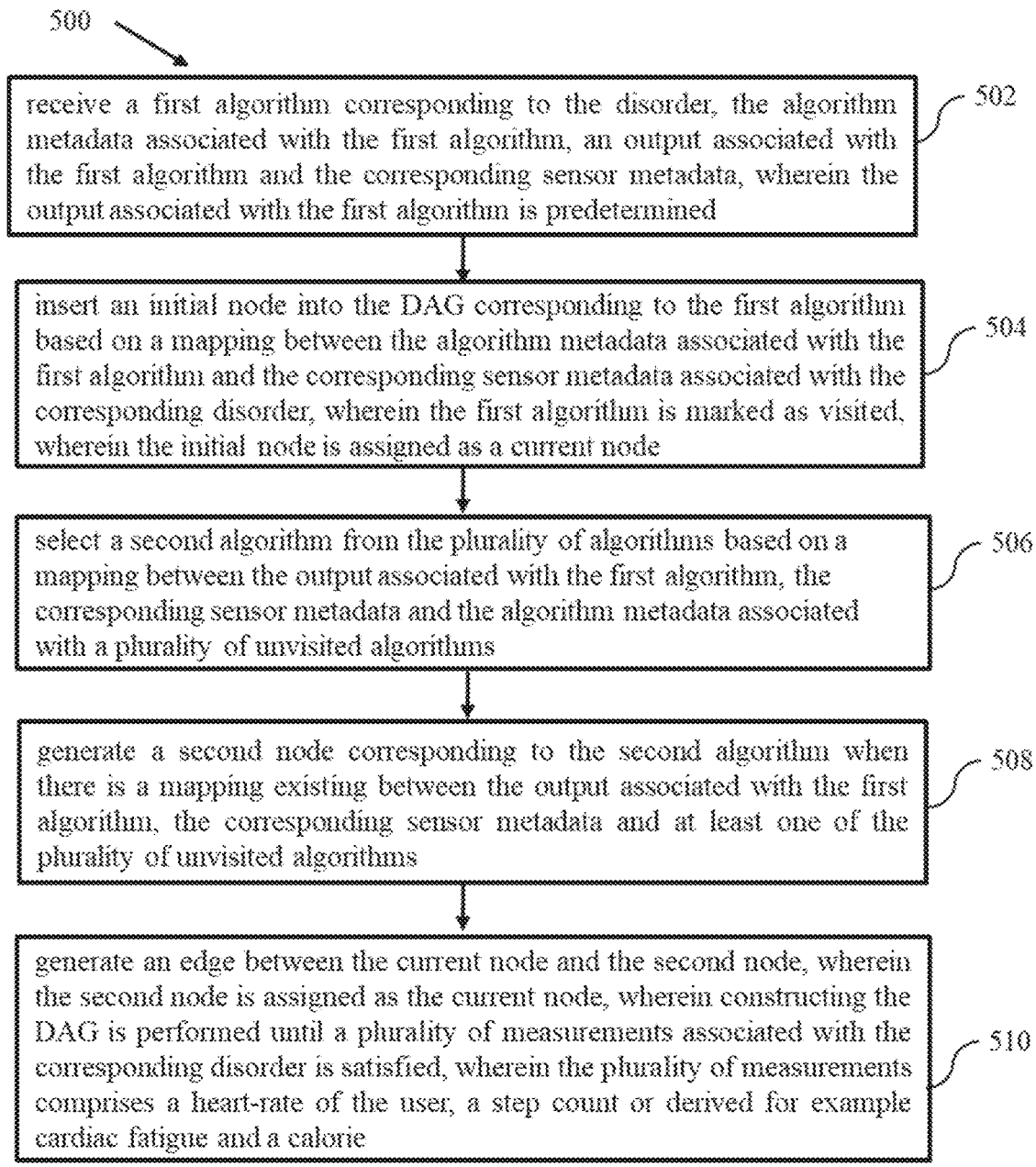
FIG. 5 is an exemplary flow diagram for a processor implemented method for constructing a Directed Acyclic Graph (DAG) in digital biomarkers platform implemented by the system of FIG. 1 according to some embodiments of the present disclosure.

In an embodiment, the method of constructing the DAG for analyzing the disorder from the plurality of disorders is explained using FIG. 5.

FIG. 5 is an exemplary flow diagram for a processor implemented method for constructing the DAG in digital biomarkers platform implemented by the system of FIG. 1 according to some embodiments of the present disclosure.

Now referring to FIG. 5, at step 502, the first algorithm corresponding to the disorder, the algorithm metadata associated with the first algorithm, an output associated with the first algorithm and the corresponding sensor metadata is received. The output associated with the first algorithm is predetermined. At step 504, an initial node is inserted into the DAG corresponding to the first algorithm based on a mapping between the algorithm metadata associated with the first algorithm and the corresponding sensor metadata associated with the corresponding disorder. The first algorithm is marked as visited. The initial node is assigned as a current node. At step 506, a second algorithm is selected from the plurality of algorithms based on a mapping between the output associated with the first algorithm, the corresponding sensor metadata and the algorithm metadata associated with a plurality of unvisited algorithms. At step 508, a second node is generated corresponding to the second algorithm when there is a mapping existing between the output associated with the first algorithm, the corresponding sensor metadata and at least one of the pluralities of unvisited algorithms. At step 510 of method 500, an edge is generated between the current node and the second node. The second node is assigned as the current node. The DAG construction is performed until a plurality of measurements associated with the corresponding disorder is satisfied. The plurality of measurements includes the heart-rate of the user, the step count or derived for example cardiac fatigue and the calorie.

Figure 6:
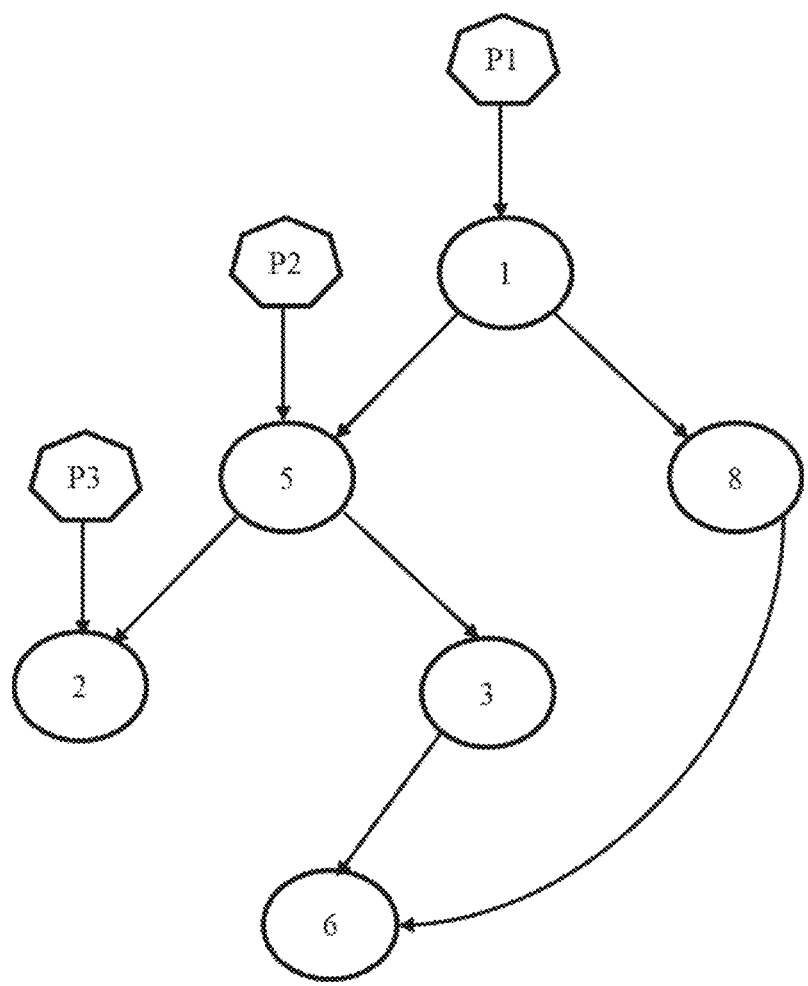
FIG. 6 is an exemplary DAG associated with the processor implemented method for digital biomarkers platform implemented by the system of FIG. 1 according to some embodiments of the present disclosure.

FIG. 6 is an exemplary DAG associated with the processor implemented method for digital biomarkers platform implemented by the system of FIG. 1 according to some embodiments of the present disclosure.

Now referring to FIG. 6, P1, P2 and P3 are primitive inputs associated with the DAG and which come from sensors or human input. The nodes 1, 5,8, 2, 3 and 6 are the corresponding algorithms. A plurality of paths associated with the DAG, for example 1→5→2, 1→5→3→6 and 1→8→6 are the paths corresponding to a plurality of disorders associated with the user. The execution of node 1 is deferred until P1 is available, execution of node 5 is deferred until P2 data is available, and similarly node 2 is deferred P3 is available. That path 1→5→2 is not completed in a single flow. Rather it has multiple entry points at different time intervals. Similarly, path 1→5→3→6 is also not completed in a single flow. The deferred processing is until P2 data is available and thereafter is straight forward path from 5→3→6. Each path in the DAG is associated with a disorder. For example, the algorithm pipeline 1→5→3→6 correspond to an identification of a heart disease and the algorithm pipeline 1→8→6 corresponds to identifying of Parkinson's disease.

The pseudocode used for DAG construction is given below:

---

Pseudocode 2: Pseudocode for DAG generation

```
function generate_graph(graph, algorithm, dependent_node)
    if graph.containes_node (algorithm) is false
        algorithm_node← graph.create_node (algorithm)
    else
        algorithm_node← graph.get_node (algorithm)
    end
    algorithm_node.add_dependent (dependent_node);
    for each dependency in algorithm.dependencies do
        graphs← generate_graph (graph, dependency, algorithm)
    end
    return graph
end
```

---

In the above pseudocode for graph generation, "algorithm" refers to current algorithm being processed, "dependent" refers to the algorithm which is dependent on current algorithm and "dependencies" are the algorithms on which the current algorithm has dependency.

The data analysis unit 114, when executed by one or more hardware processors 102 of the system 100 analyze the disorder associated with the user based on the selected algorithm pipeline.

In an embodiment, considering the selected algorithm pipeline 1→8→6 corresponding to identifying of Parkinson's disease, the algorithm 1 corresponding to the node 1 is a "balance score generator_1", computing a balance score from the wrist wearable device and the corresponding sensor inputs are the accelerometer, the gyroscope and the barometer. The output associated with the algorithm 1 is a "first Balance Score". The balance score is a numeric value indicating how stable person is while standing/walking etc. Further, the algorithm 8 corresponding to the node 8 is a "balance score generator_2" which computes balance score based on the Kinect® depth camera. The inputs for the algorithm 8 are Skeletal Joint Data (Head, Neck, Arm, Elbow, Wrist, etc—each joint has x, y, z) from the Kinect® depth camera. The output is a "second balance score". Further, the algorithm 6 corresponding to the node 6 is a "fall prediction" algorithm which takes time series data from at least one of the first balance score and a second balance score as input. The output associated with the algorithm 6 is a numeric value indicating the chance of falling.

Figure 7:
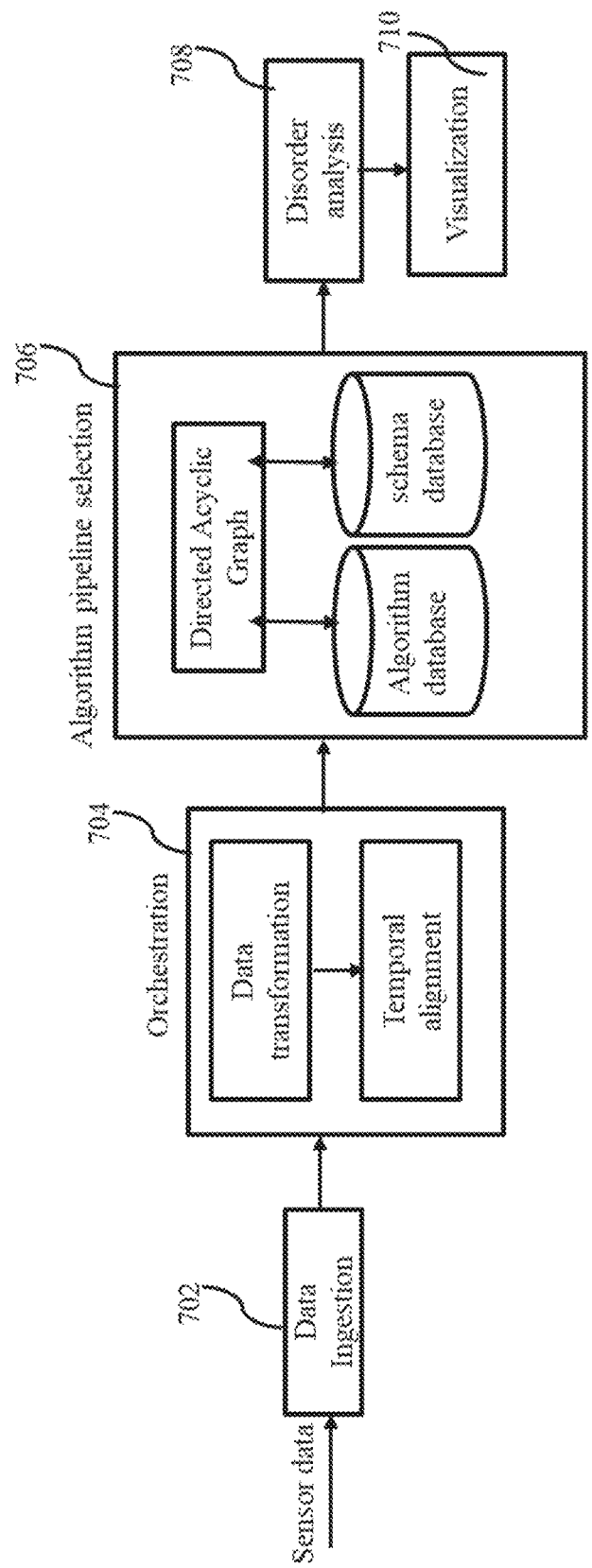
FIG. 7 is an exemplary architecture for a processor implemented method for digital biomarkers platform implemented by the system of FIG. 1 according to some embodiments of the present disclosure.

FIG. 7 is an exemplary architecture for a processor implemented method for digital biomarkers platform implemented by the system of FIG. 1 according to some embodiments of the present disclosure.

Now, referring to FIG. 7, the architecture includes, the data ingestion module 702, the data orchestration module 704, the algorithm pipeline selection module 706, the disorder analysis module 708 and the visualization module 710. The data ingestion module 702 receives the raw data from a plurality of heterogenous sensors associated with wrist wearable device of the user or a patient. The data orchestration module 704 receives the raw data from the data ingestion module 702 and performs data transformation and temporal alignment of the transformed data. The temporally aligned data is provided as input to the algorithm pipeline selection module 706. The algorithm pipeline corresponding to the disorder to be analyzed is obtained using the method described in paragraph 50 using the DAG, algorithm database and the schema database or metadata database. The DAG associated with the algorithm pipeline selection module 706 is constructed by using the method as explained in paragraph 53. Further, the disorder analysis module analyzes the disorder associated with the user using the selected algorithm pipeline. The visualization module 710 provides visualization of the meta information and can be used for visualizing data at both sensor as well as processing level. In some embodiment, the data visualization is performed in the sensor level and in some other embodiment, the data can be visualized in processing level. The visualization is performed using the metadata associated with the corresponding data.

Further, the present disclosure implements and uses specialized algorithms for data analysis. It offers algorithm as a service design which is analogous to where each algorithm is packaged and containerized as an independent standalone service. The plurality of algorithms associated with the architecture as explained in FIG. 7 are uniquely discoverable and scalable, thus enabling the algorithms to be pluggable.

In an embodiment, the sensors capture the raw data and buffers data according to its buffering capacity before transferring it to the data ingestion module 702. In an embodiment, the device buffers and transfers the data in batches of duration of 10 seconds. These batches may arrive out of order at the data ingestion module 702 due to network latency or may not arrive at all. However, the present disclosure is needs data of at least 2 seconds of records per chunk.

Hence the orchestration module 704 uses algorithm meta information and partitions the input batches of data into 24 slots for each hour of the day. The orchestration module in it's preprocessing step checks for contiguity and gaps in data chunks. Unprocessed contiguous chunks in a given slot are ordered by time and merged together to form larger unprocessed document, which is then passed on to the algorithm for processing. Noncontiguous chunks are independently passed to the algorithm for processing. Finally, the processed data is merged as per 24 hour slots and stored in the database.

In an embodiment, the plurality of algorithms used in the method disclosed herein are developed in Java, however the algorithm developers may have different preferences with respect to choose of development language, execution environment and/or use of available open source libraries. Hence, containerization helps package these algorithms with respective choice of development language, execution environment and necessary dependencies, thereby giving freedom to the algorithm developers. But, the difference in development language and execution environment poses integration challenge. To overcome this, there required is a common and consistent interface for accessing these algorithms. Thus, light-weight application are created as a wrapper to the algorithms to provide a consistent interface.

In an embodiment, the step count accuracy of the present disclosure is experimented as follows: A total of ~4000 steps spread over 16 different sessions from multiple users wearing a Samsung Galaxy Watch Active2® smartwatch is collected. Users performed natural walking in an indoor environment with curved trajectories and multiple U-turns. Table I shows results for some of the walking sessions. It can be seen that for all the sessions, the present disclosure performs better in detecting the number of steps. An average error of 4.6 steps per session is observed (for an average total no. of 240 steps per session).

TABLE I

| Ground Truth | U-Turns | Step Count Error of the present disclosure |
|---|---|---|
| 200 | 17 | 5 |
| 351 | 29 | 5 |
| 311 | 26 | 4 |

In an embodiment, the robustness towards the false detection of steps is analyzed as follows: As observed in the previous paragraphs, step count reported by commercial wearables can be inaccurate in indoor environment, with mis-detection of steps from the sensor signal while performing non-walking Activities of Daily Livings (ADLs). In order to establish the resilience of our step-detection method, various ADLs were performed while wearing the smartwatch like getting up, sitting down, wearing shoes, changing clothes, washing hands, eating, working on laptop etc. during multiple sessions. Table II shows false step counts accumulated during these sessions the present disclosure and shows appreciably better robustness towards false step counts. As can be expected, most of the false counts were accumulated during activities with relatively higher powered acceleration signal for periods exceeding~10s, like changing clothes, and quick movements like tying shoes. For activities with lower intensities like texting, writing on paper, sitting down/getting up etc., none of the solutions produced any false steps.

TABLE II

| Session Duration | False Steps Counted for the present disclosure |
|---|---|
| 15 mins | 8 |
| 10 mins | 15 |
| 13 mins | 21 |
| 15 mins | 23 |

In an embodiment, the short walking spells of the present disclosure is analyzed as follows: As discussed in previous section, detection of true steps in indoor scenarios is challenged by the ADLs. In addition, indoor walking is usually limited to ambulation from one room to another. Such spells of short walking are a challenge for step detection, and sessions with 10 steps or less can go undetected by the device. In order to establish our method's efficiency in detecting such short spells, various sessions of discontinuous walking indoors moving from one room to another were performed. In a single session, multiple such walks were performed with the number of steps in a certain range. Table III shows step-count errors incurred by the present disclosure for multiple sessions.

TABLE III

| Steps Range | Ground Truth Steps | Step Count Error: Proposed |
|---|---|---|
| 8-15 | 124 | 20 |
| 10-15 | 156 | 2 |
| 15-20 | 206 | 7 |
| 8-20 | 156 | 2 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address the unresolved problem of gathering and analyzing important insights into the health of subjects using Digital Bio-Markers platform. The platform has in-built capability for multi-vendor device and algorithm integration and the data-store can be used to build corpus of data for research purpose. An improved step detection algorithm is also discussed for a better detection in indoor scenarios, robustness against false detections while performing ADLs, and an effective detection of short spells of indoor walks.

Further, the present disclosure is implemented based on empathy maps created through interviews with physicians and patients. The present disclosure provides clear and easy way to understand health information for the patients and at the same time it provides insights into patient's health to the physicians. Further, the present disclosure provides a unified view of digital human health data to both patients and physicians It is to be understood that the scope of the protection is extended to such a program and in addition to a computer-readable means having a message therein such computer-readable storage means contain program-code means for implementation of one or more steps of the method when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs, GPUs and edge computing devices.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e. non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:
receiving, by one or more hardware processors, a raw data from a plurality of sensors associated with a user, wherein the plurality of sensors are heterogeneous;
transforming, by the one or more hardware processors, the raw data corresponding to each of the plurality of sensors into a sensor metadata format associated with a corresponding sensor among the plurality of sensors;
obtaining, by the one or more hardware processors, a temporally aligned data by performing a time based slotting on the transformed data;
obtaining, by the one or more hardware processors, the sensor metadata corresponding to the temporally aligned data from a database based on a mapping between the temporally aligned data and the sensor metadata;
selecting, by the one or more hardware processors, an algorithm pipeline corresponding to a disorder to be analyzed from a Directed Acyclic Graph (DAG), wherein the selection is based on the sensor metadata and a plurality of algorithm metadata corresponding to a plurality of algorithms stored in an algorithm database, wherein selecting the algorithm pipeline corresponding to the selected disorder to be analyzed from the DAG based on the sensor metadata and a plurality of algorithm metadata comprises:
receiving the DAG comprising a plurality of nodes and a plurality of edges, wherein each of the plurality of nodes associated with the DAG represents an algorithm from the plurality of algorithms and each of the plurality of edges connecting two nodes indicates a dependency between a preceding node and a succeeding node, wherein the DAG is associated with at least one entry point;

selecting an initial node corresponding to a first algorithm of the algorithm pipeline from the DAG based on a comparison between the corresponding sensor metadata and an algorithm metadata associated with each of the plurality of algorithms, wherein the initial node is assigned as a current node;

obtaining the algorithm metadata associated with a plurality of next nodes associated with the current node;

selecting a next node from the plurality of next nodes based on a comparison between an output associated with the current node and the algorithm schema associated with each of the plurality of next nodes, wherein the selected next node is assigned as the current node, and wherein the DAG is traversed until reaching a leaf node identified based on a next null pointer; and obtaining the algorithm pipeline based on the traversal path from the initial node to the leaf node; and analyzing, by the one or more hardware processors, the disorder associated with the user based on the selected algorithm pipeline.

2. The method of claim 1, wherein constructing the DAG for a disorder from a plurality of disorders comprises:

receiving a first algorithm corresponding to the disorder, the algorithm metadata associated with the first algorithm, an output associated with the first algorithm and the corresponding sensor metadata, wherein the output associated with the first algorithm is predetermined;

inserting an initial node into the DAG corresponding to the first algorithm based on a mapping between the algorithm metadata associated with the first algorithm and the corresponding sensor metadata associated with the corresponding disorder, wherein the first algorithm is marked as visited, and wherein the initial node is assigned as a current node;

selecting a second algorithm from the plurality of algorithms based on a mapping between the output associated with the first algorithm, the corresponding sensor metadata and the algorithm metadata associated with a plurality of unvisited algorithms;

generating a second node corresponding to the second algorithm when there is a mapping existing between the output associated with the first algorithm, the corresponding sensor metadata and at least one of the plurality of unvisited algorithms; and generating an edge between the current node and the second node, wherein the second node is assigned as the current node, wherein constructing the DAG is performed until a plurality of measurements associated with the corresponding disorder is satisfied, wherein the plurality of measurements comprises a heart-rate of the user, a step count and a calorie.

3. The method of claim 1, wherein the raw data format comprises a time series data, a comma separated values, a string data, a numerical, a Boolean data, a list, a plurality of objects, a plurality of videos and a plurality of images.

4. The method of claim 1, wherein the algorithm metadata comprising a data format, a preferred sampling rate, a minimum quantum of data needed for processing, an output data format, a description of method used by the corresponding algorithm.

5. The method of claim 1, wherein the sensor metadata comprises a type of data generated by the corresponding sensor, a sampling frequency, a buffering capacity and a model associated with the corresponding sensor.

6. A system comprising:
at least one memory storing programmed instructions; one or more Input/Output (I/O) interfaces; and one or more hardware processors operatively coupled to the at least one memory, wherein the one or more hardware processors are configured by the programmed instructions to:

receive a raw data from a plurality of sensors associated with a user, wherein the plurality of sensors are heterogeneous;

transform the raw data corresponding to each of the plurality of sensors into a sensor metadata format associated with a corresponding sensor among the plurality of sensors;

obtain a temporally aligned data by performing a time based slotting on the transformed data;

obtain the sensor metadata corresponding to the temporally aligned data from a database based on a mapping between the temporally aligned data and the sensor metadata;

select an algorithm pipeline corresponding to a disorder to be analyzed from a Directed Acyclic Graph (DAG), wherein the selection is based on the sensor metadata and a plurality of algorithm metadata corresponding to a plurality of algorithms stored in an algorithm database, wherein selecting the algorithm pipeline corresponding to the selected disorder to be analyzed from the DAG based on the sensor metadata and a plurality of algorithm metadata comprises:

receiving the DAG comprising a plurality of nodes and a plurality of edges, wherein each of the plurality of nodes associated with the DAG represents an algorithm from the plurality of algorithms and each of the plurality of edges connecting two nodes indicates a dependency between a preceding node and a succeeding node, wherein the DAG is associated with at least one entry point;

selecting an initial node corresponding to a first algorithm of the algorithm pipeline from the DAG based on a comparison between the corresponding sensor metadata and an algorithm metadata associated with each of the plurality of algorithms, wherein the initial node is assigned as a current node;

obtaining the algorithm metadata associated with a plurality of next nodes associated with the current node;

selecting a next node from the plurality of next nodes based on a comparison between an output associated with the current node and the algorithm schema associated with each of the plurality of next nodes, wherein the selected next node is assigned as the current node, and wherein the DAG is traversed until reaching a leaf node identified based on a next null pointer; and obtaining the algorithm pipeline based on the traversal path from the initial node to the leaf node, wherein constructing the DAG for a disorder from a plurality of disorders comprises:

receiving a first algorithm corresponding to the disorder, the algorithm metadata associated with the first algorithm, an output associated with the first algorithm and the corresponding sensor metadata, wherein the output associated with the first algorithm is predetermined;

inserting an initial node into the DAG corresponding to the first algorithm based on a mapping between the algorithm metadata associated with the first algorithm and the corresponding sensor metadata associated with the corresponding disorder, wherein the first algorithm is marked as visited, and wherein the initial node is assigned as a current node;

selecting a second algorithm from the plurality of algorithms based on a mapping between the output associated with the first algorithm, the corresponding sensor metadata and the algorithm metadata associated with a plurality of unvisited algorithms;

generating a second node corresponding to the second algorithm when there is a mapping existing between the output associated with the first algorithm, the corresponding sensor metadata and at least one of the plurality of unvisited algorithms; and generating an edge between the current node and the second node, wherein the second node is assigned as the current node, wherein constructing the DAG is performed until a plurality of measurements associated with the corresponding disorder is satisfied, wherein the plurality of measurements comprises a heart-rate of the user, a step count and a calorie; and analyze the disorder associated with the user based on the selected algorithm pipeline.

7. The system of claim 6, wherein the raw data format comprises a time series data, a comma separated values, a string data, a numerical, a Boolean data, a list, a plurality of objects, a plurality of videos and a plurality of images.

8. The system of claim 6, wherein the algorithm metadata comprising a data format, a preferred sampling rate, a minimum quantum of data needed for processing, an output data format, a description of method used by the corresponding algorithm.

9. The system of claim 6, wherein the sensor metadata comprises a type of data generated by the corresponding sensor, a sampling frequency, a buffering capacity and a model associated with the corresponding sensor.

10. One or more non-transitory machine-readable information storage mediums comprising one or more instructions which when executed by one or more hardware processors cause:

receiving, by one or more hardware processors, a raw data from a plurality of sensors associated with a user, wherein the plurality of sensors are heterogeneous;

transforming, by the one or more hardware processors, the raw data corresponding to each of the plurality of sensors into a sensor metadata format associated with a corresponding sensor among the plurality of sensors;

obtaining, by the one or more hardware processors, a temporally aligned data by performing a time based slotting on the transformed data;

obtaining, by the one or more hardware processors, the sensor metadata corresponding to the temporally aligned data from a database based on a mapping between the temporally aligned data and the sensor metadata;

selecting, by the one or more hardware processors, an algorithm pipeline corresponding to a disorder to be analyzed from a Directed Acyclic Graph (DAG), wherein the selection is based on the sensor metadata and a plurality of algorithm metadata corresponding to a plurality of algorithms stored in an algorithm database, wherein selecting the algorithm pipeline corresponding to the selected disorder to be analyzed from the DAG based on the sensor metadata and a plurality of algorithm metadata comprises:

receiving the DAG comprising a plurality of nodes and a plurality of edges, wherein each of the plurality of nodes associated with the DAG represents an algorithm from the plurality of algorithms and each of the plurality of edges connecting two nodes indicates a dependency between a preceding node and a succeeding node, wherein the DAG is associated with at least one entry point;

selecting an initial node corresponding to a first algorithm of the algorithm pipeline from the DAG based on a comparison between the corresponding sensor metadata and an algorithm metadata associated with each of the plurality of algorithms, wherein the initial node is assigned as a current node;

obtaining the algorithm metadata associated with a plurality of next nodes associated with the current node;

selecting a next node from the plurality of next nodes based on a comparison between an output associated with the current node and the algorithm schema associated with each of the plurality of next nodes, wherein the selected next node is assigned as the current node, and wherein the DAG is traversed until reaching a leaf node identified based on a next null pointer; and obtaining the algorithm pipeline based on the traversal path from the initial node to the leaf node, wherein constructing the DAG for a disorder from a plurality of disorders comprises:

receiving a first algorithm corresponding to the disorder, the algorithm metadata associated with the first algorithm, an output associated with the first algorithm and the corresponding sensor metadata, wherein the output associated with the first algorithm is predetermined;

inserting an initial node into the DAG corresponding to the first algorithm based on a mapping between the algorithm metadata associated with the first algorithm and the corresponding sensor metadata associated with the corresponding disorder, wherein the first algorithm is marked as visited, and wherein the initial node is assigned as a current node;

selecting a second algorithm from the plurality of algorithms based on a mapping between the output associated with the first algorithm, the corresponding sensor metadata and the algorithm metadata associated with a plurality of unvisited algorithms;

generating a second node corresponding to the second algorithm when there is a mapping existing between the output associated with the first algorithm, the corresponding sensor metadata and at least one of the plurality of unvisited algorithms; and generating an edge between the current node and the second node, wherein the second node is assigned as the current node, wherein constructing the DAG is performed until a plurality of measurements associated with the corresponding disorder is satisfied, wherein the plurality of measurements comprises a heart-rate of the user, a step count and a calorie; and analyzing, by the one or more hardware processors, the disorder associated with the user based on the selected algorithm pipeline.

11. The one or more non-transitory machine-readable information storage mediums of claim 10, wherein the raw data format comprises a time series data, a comma separated values, a string data, a numerical, a Boolean data, a list, a plurality of objects, a plurality of videos and a plurality of images.

12. The one or more non-transitory machine-readable information storage mediums of claim 10, wherein the algorithm metadata comprising a data format, a preferred sampling rate, a minimum quantum of data needed for processing, an output data format, a description of method used by the corresponding algorithm.

13. The one or more non-transitory machine-readable information storage mediums of claim 10, wherein the sensor metadata comprises a type of data generated by the corresponding sensor, a sampling frequency, a buffering capacity and a model associated with the corresponding sensor.

\* \* \* \* \*